US009375294B2

(12) United States Patent
Schwenter et al.

(10) Patent No.: US 9,375,294 B2
(45) Date of Patent: Jun. 28, 2016

(54) METHOD FOR PRODUCING IMPLANTS

(75) Inventors: Peter Schwenter, Gerlafingen (CH); Peter Perler, Port (CH); Roger Staudenmann, Busswil b. Buren (CH); Jörg Mayer, Niederlenz (CH); Andrea Mueller, Winterthur (CH); Urs Weber, Olten (CH)

(73) Assignees: NEW DENT AG, Oensingen (CH); WOODWELDING AG, Stansstad (CH)

( * ) Notice: Subject to any disclaimer, the term of this patent is extended or adjusted under 35 U.S.C. 154(b) by 875 days.

(21) Appl. No.: 13/514,099

(22) PCT Filed: Dec. 7, 2010

(86) PCT No.: PCT/CH2010/000307
§ 371 (c)(1),
(2), (4) Date: Aug. 1, 2012

(87) PCT Pub. No.: WO2011/069271
PCT Pub. Date: Jun. 16, 2011

(65) Prior Publication Data
US 2012/0292815 A1    Nov. 22, 2012

(30) Foreign Application Priority Data
Dec. 11, 2009    (CH) ........................................ 1906/09

(51) Int. Cl.
*B29C 33/12*    (2006.01)
*A61C 8/00*     (2006.01)
*A61C 13/00*    (2006.01)

(52) U.S. Cl.
CPC ............. *A61C 8/0012* (2013.01); *A61C 8/0016* (2013.01); *A61C 13/0003* (2013.01)

(58) Field of Classification Search
CPC ........................... B29C 33/123; B29C 37/0082
See application file for complete search history.

(56) References Cited

U.S. PATENT DOCUMENTS

| 5,679,299 | A | * | 10/1997 | Gilbert et al. | ................. 264/103 |
| 5,952,397 | A | * | 9/1999 | Fujiki et al. | ..................... 522/99 |
| 2007/0222114 | A1 | * | 9/2007 | Ziran et al. | .................... 264/279 |

FOREIGN PATENT DOCUMENTS

| JP | H02209148 | 8/1990 |
| JP | H06125979 | 5/1994 |
| JP | H08131460 | 5/1996 |
| JP | 2000072572 | 3/2000 |
| JP | 2007522847 | 8/2007 |
| JP | 2009254808 | 11/2009 |
| WO | 97/33017 | 9/1997 |
| WO | 2004/017857 | 3/2004 |
| WO | 2008/036034 | 3/2008 |

* cited by examiner

*Primary Examiner* — Joseph S Del Sole
*Assistant Examiner* — John Robitaille
(74) *Attorney, Agent, or Firm* — Rankin, Hill & Clark LLP

(57) ABSTRACT

A method for producing an implant including the following steps is provided: —providing a core element having a first material; —providing a negative mold of the implant; —inserting the core element and at least one anchoring element made of a second material into the negative mold, wherein the second material is thermoplastic, —closing the negative mold and applying an elevated deformation temperature, wherein at the deformation temperature the second material is plastically deformable, viscous, or liquid and the first material is solid, —cooling the negative mold together with the core element and the anchoring element, and—removing the resulting implant from the core element and the anchoring element from the negative mold.

12 Claims, 2 Drawing Sheets

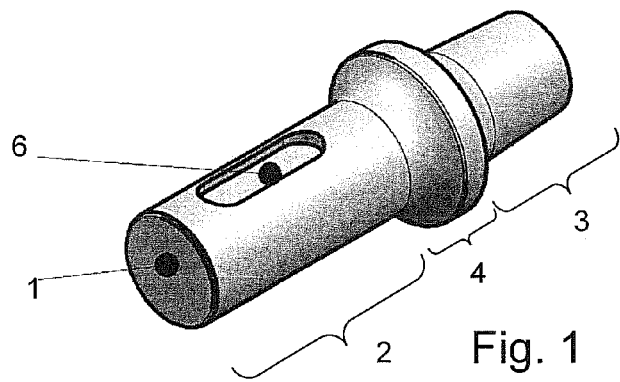
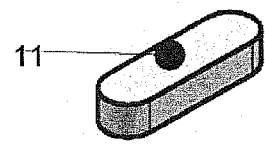
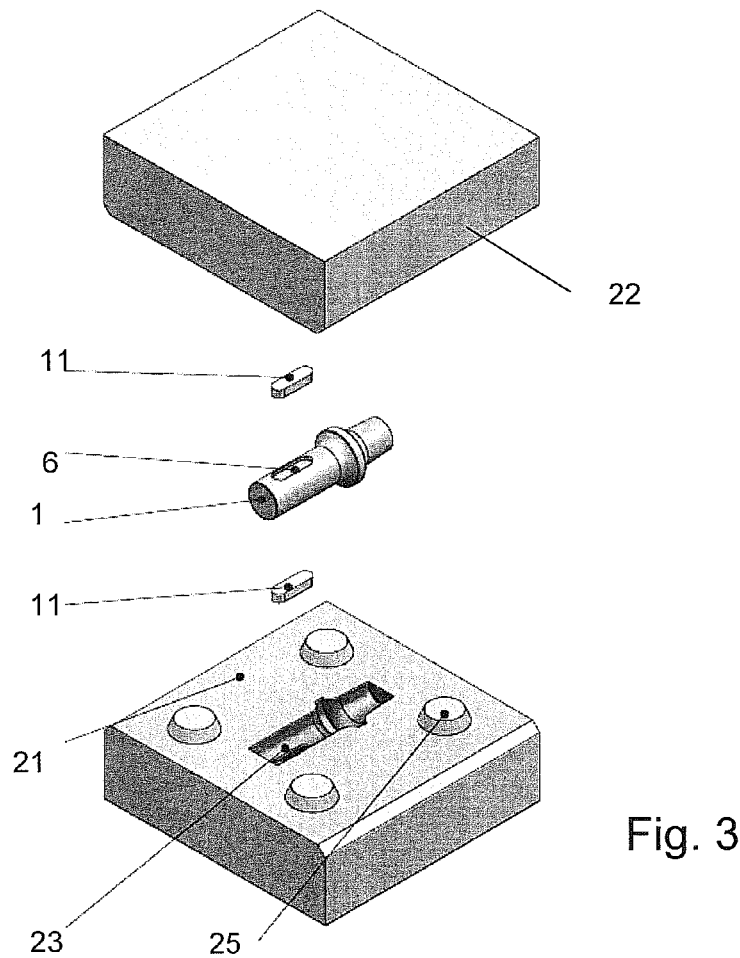

METHOD FOR PRODUCING IMPLANTS

BACKGROUND OF THE INVENTION

1. Field of the Invention

The invention lies in the field of medical engineering and relates to an implant, more particularly a dental implant. In particular, it relates to a method for producing hybrid implants with an e.g. metallic or ceramic core and at least one component forming part of the surface.

2. Description of Related Art

Implants which comprise a core and a coating made of a biocompatible and, in the initial state, polymer material have been disclosed by e.g. DE 20 2004 009 060. According to the teaching of this document, a polymer film is applied by adhesive bonding, shrinking, varnishing, spraying, dip coating, etc. and subsequently carbonized in an oxygen-free atmosphere.

Implants with a hard core and a coating made of a polymer material have also been disclosed in WO 97/33017. According to this document, PMMA in the form of fibers with molecule chains oriented in the longitudinal direction is wound around the core, and the cover created in the process is heated so that the fibers contract and are interconnected. The heating can take place with simultaneous application of pressure.

Implants with surface regions made of a thermoplastic material and a core made of a material that is different from this thermoplastic material have for example been disclosed in U.S. Pat. No. 7,008,226. Mechanical vibrations are coupled into such implants during an implantation as intended. The mechanical energy from these vibrations is converted into thermal energy in the thermoplastic material where high concentrations of stress occur. The thermoplastic material melts locally and is pressed into cavities and/or other structures of the surrounding tissue by means of pressure exerted during the implantation. After the mechanical vibrations are switched off, the thermoplastic material solidifies, and this forms an interlocking fit with the structures of the tissue.

Structures of the thermoplastic material that have been applied in a targeted fashion, which form points with high concentrations of stress, are often referred to as "energy direction transmitters". Such energy direction transmitters are often present in the form of edges, tips and similar geometric structures. The mechanical workability of such geometric structures is limited, particularly in the case of advanced miniaturization. Thus, the problem arises of how thermoplastic elements with these structures can be attached to a core made of another material.

BRIEF SUMMARY OF THE INVENTION

Accordingly, one object of the invention is to provide a method for producing an implant with a core made of a first material and at least one anchoring element which forms a surface region of the implant and is made of a second, thermoplastic material, which invention is suitable even if the anchoring element comprises fine structures.

According to one aspect of the invention, a method for producing an implant comprises the following steps:
 providing a core element of a first material;
 providing a negative mold of the implant;
 introducing the core element and at least one anchoring element made of a second material into the negative mold, wherein the second material is thermoplastic,
 sealing the negative mold and applying an elevated deformation temperature, wherein, at the deformation temperature, the second material is plastically deformable, viscous or liquid and the first material is solid,
 cooling the negative mold with the core element and the anchoring element, and
 removing the resulting implant, which is made from the core element and the anchoring element, from the negative mold.

Here, an "elevated temperature" is a temperature that is higher than room temperature and preferably also higher than the body temperature at which the implant will be implanted at a later stage, i.e. more particularly higher than 37° C. To the extent that a glass transition temperature is defined for the second material, the elevated temperature is preferably above the glass transition temperature. It can be below the liquefaction temperature. A particularly preferred temperature range is a temperature of significantly above the glass transition temperature—e.g. by at least a quarter or at least a third of the difference between the liquefaction and glass transition temperatures—but lying below the liquefaction temperature. Depending on the material composition of the second element, it may be advantageous for the deformation temperature to be closer to the liquefaction temperature than to the glass transition temperature.

It may be advantageous to select the materials and the deformation temperature such that the method is carried out with at least one initially solid anchoring element, which is pasty and dough-like at the deformation temperature.

The deformation temperature need not be constant but may have a temperature profile; in this case, the statements made above in respect of the elevated temperature apply to the maximum temperature.

Elevated pressure, i.e. pressure above atmospheric pressure, is preferably also applied during the application of the elevated temperature. By way of example, the negative mold can have two or more mold parts which complete one another to form the negative mold; these mold parts are pressed against one another, either by means of a suitable mechanical system or by applying a weight on a mold part situated at the top; pneumatic, hydrostatic or hydraulic or other means are also feasible for applying a pressure to the mold internal cavity.

The anchoring element is/the anchoring elements are deformed at the deformation temperature and under pressure, as a result of which it is also possible to form very fine energy direction transmitters. At the same time, the at least one anchoring element connects with the core element. It was found that the resultant connection is particularly intimate and secure.

According to one aspect of the invention, the liquefiable material in form of at least one anchoring element is, thus, inserted into the negative mold and not, for example, formed-on in the initial liquid state by insert molding around the core element. This has huge advantages because it is well known that the instruments—injection molding machine, injection mold—required for such insert molding are very complicated and expensive. Moreover, the heating and cooling phases and, optionally, a holding phase can be driven at will; unlike an injection molding method there is no predetermined cycle time. Targeted slow processing also affords the possibility of not freezing stresses into the liquefiable material. The method according to this aspect of the invention also enables the use of an elastic mold. Firstly, this is advantageous in that, unlike for injection-molding tools, there is no need for high precision in the dimensioning and positioning of sealing edges for good sealing of the mold. Secondly, the risk of damaging brittle core elements—made of ceramics, for example—is reduced if these are used.

Then, by way of example, a mold can then be denoted as "elastic" if a noticeable elastic deformation compared to the characteristic dimensions of structures on the implant surface can be brought about in the case of the prevalent forces. In particular, the elastic deformation can at least in part be traced back to entropy elasticity and/or the negative mold can be manufactured from an elastomer or (another) plastic.

In embodiments, core element, anchoring element(s) and negative mold are matched to one another such that the negative mold is in direct contact with the core-element surface during the process, i.e. while the negative mold surrounds the core element and the anchoring element(s), for example such that the common contact surface is under mechanical pressure.

Even apart from the usability of an elastic mold, the requirements in respect of the dimensional accuracy, the mismatch in mold and the exactness of the geometry are significantly lower than in the case of the injection molding method; nevertheless, even very fine structures can be formed-on in the liquefiable material.

A further possible advantage of embodiments of the invention lies in material sparing. In general, a pasty state below the liquefaction temperature of the liquefiable material is enough for reshaping and adhesion. Thus, discoloration or even disintegration of the material can be avoided in many cases. The method is easy to control. It is suitable for individual parts and small batches, and also for relatively large batches.

In embodiments, the mold (negative mold) is held at the deformation temperature during a holding time. In some embodiments, the cooling can be in a controlled, slow fashion in addition or as an alternative thereto.

The first material—i.e. the material of the core element—can be a metal—e.g. titanium or a titanium-based substance—a ceramic substance, e.g. zirconium oxide or a zirconium oxide-based substance, or else an optionally strengthened thermosetting polymer or an optionally strengthened thermoplastic polymer with a higher liquefaction temperature than the second material. Of course, it is also feasible for the core element itself to be a hybrid of many materials, i.e. the fact that the core element has a first material does not preclude the presence of further materials. By way of example, the core element itself can have a metallic core pin and a cladding on ceramic or polymer basis.

By way of example, the second material is a material based on a thermoplastic polymer. It can be an absorbable or non-absorbable thermoplastic polymer, optionally with additives. By way of example, specific examples of suitable materials are found in WO 2008/095 327, in particular on pages 16-18, with reference explicitly being made here to the teaching thereof in respect of utilizable liquefiable materials; however, materials that are not mentioned in this document (single-phase materials or composites) are also feasible, which materials can be liquefied under the influence of mechanical energy, more particularly mechanical vibrations, and re-solidify after the energy influx is stopped.

Preferably, two or more anchoring elements are present, which remain separate, i.e. do not flow into one another, during and after the deformation and/or bonding process (i.e. while they are situated in the negative mold and exposed to an elevated temperature). However, it is also possible for only one contiguous anchoring element to be present or for a plurality of initially separate anchoring elements to be fused together during the deformation and/or bonding process.

By way of example, the anchoring element or anchoring elements is/are inherently dimensionally stable and, in the process, is/are preferably corporeal, compact elements.

In preferred embodiments, the implant—or an endosseous region thereof—has surface regions made of the first material and surface regions made of the second material, which, for example, are both arranged such that they both come into contact with bone tissue after the implantation. By way of example, there may be a plurality of anchoring elements which are not contiguous, even after the production method is complete. More particularly, provision can be made for the anchoring elements not to enclose the core in a cladding-like manner. If an implant/implantation axis is defined (like, for example, in a dental implant or another implant which is pin-like in regions), the anchoring elements in embodiments are more particularly arranged such that in at least one plane perpendicular to the implantation axis, both surface regions made of the first material and surface regions made of the second material are present along a circumferential line.

The core element preferably comprises at least one recess—for example one recess per anchoring element—into which the corresponding anchoring element is inserted and in which the anchoring element is anchored such that it projects beyond an outer contour of the core element. At its base, the recess can form a defined, for example planar, support for the anchoring element. It can have the shape of a slot, a rectangular pocket, a circular pocket, a polygonal pocket, an elliptical pocket, a pocket approximating one of these shapes or any other shape. Moreover, the recesses can also have undercuts in order, additionally, to connect the anchoring element with the core element by means of a geometric interlocking fit.

The contact face between the core element and the anchoring element or anchoring elements—i.e. the base of the recess for example—can be treated prior to the deformation and/or bonding process in order to improve the adhesion. By way of example, this can be brought about by sandblasting, shot peening, etching, laser treating or other surface-modifying, stripping and/or else coating methods. The anchoring element and/or, depending on composition, the core element as well can be activated by plasma and/or by a primer for improving the adhesion.

The utilized negative mold comprises at least two mold parts, which can be positioned with respect to one another such that this results in an interior cavity of the desired implant shape. Positioning aids can be present on the mold parts, the former engaging into one another when the mold parts are brought together such that the relative position is defined. Pressure in the form of a directed force can be exerted particularly in the case of embodiments with a positioning aid—the mold parts are pressed against one another. Weight is an example of such a directed force.

The negative mold is elastic, preferably at least in the region of the boundary between the mold parts, and can, for example, wholly consist of an elastic material. Moreover, compared to an injection mold, the negative mold can be comparatively soft, with a hardness of, for example, between 20 Shore OO and 100 Shore D, more particularly between 10 Shore A and 80 Shore D, between 10 and 100 Shore A or between 10 and 60 Shore A, particularly preferably between 15 and 40 Shore A. Possible materials for the negative mold include, inter alia, silicones, but also other elastic materials that readily withstand the deformation temperature, for example polyurethane, nitrile rubber, etc.

BRIEF DESCRIPTION OF THE DRAWINGS

In the following, exemplary embodiments of the invention are explained in more detail on the basis of figures. The figures are not true to scale. In the figures, the same reference signs denote the same or analogous elements. In detail:

FIG. 1 shows an illustration of a core element;

FIG. 2 shows an illustration of an anchoring element before the deformation and/or bonding process;

FIG. 3 shows an exploded view of the core element, two anchoring elements and a negative mold for carrying out the method, before the deformation and/or bonding process;

DETAILED DESCRIPTION OF THE INVENTION

Figure 4:
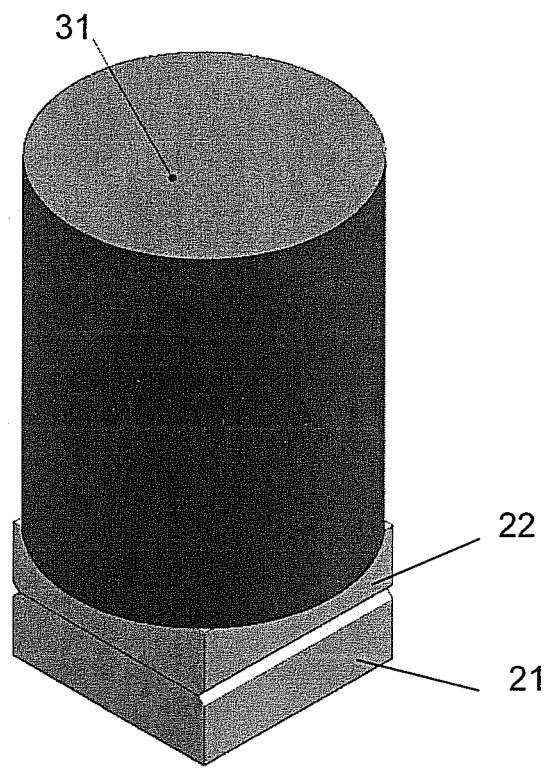
FIG. 4 shows the negative mold in the closed state and under pressure.

The core element 1 as per FIG. 1 for forming a dental implant has, in a manner known per se, an anchoring section 2, which is anchored in the bone in the implanted state, and an assembling section 3, integral therewith, for attaching a crown or another element. A widening 4 is formed in the transition region, the former being able, for example, to form a sealing shoulder, which is supported on the gum, after the implantation. A person skilled in the art will readily identify that the teaching of the present invention can readily be applied to other implant molds for dental implants—also including implant molds for two-part systems with a separate abutment—and to further, non-dental implants which can be implanted by means of mechanical energy and under at least partial liquefaction of a liquefiable material of the implant.

By way of example, the core element is manufactured from a titanium substance or a ceramic substance, for example on the basis of zirconium oxide.

Two slot-like recesses 6 are present in the region of the anchoring section 2 (only one of the recesses is visible in the figure; the second recess is situated in the region, lying opposite to the first recess, that is not visible in the figure). The base of this recess is roughened. The remaining endosseous surface region (i.e. the surface region of the anchoring section that is surrounded by bone tissue in the implanted state) can also be roughened at least in sections, with the roughness of this remaining surface region being optimized for the purposes of osseointegration; the mean depth of the roughening in this remaining surface region is e.g. between 1 μm and 10 μm, the maximum depth of the roughening is e.g. between 3 μm and 15 μm.

The anchoring element 11 as per FIG. 2 has, in the illustrated initial state, a shape matched to the shape of the slot 6 with a thickness that is greater than the depth of the slot. Specific structures like energy direction transmitters or the like need not be present.

By way of example, the anchoring element 11 is manufactured from an absorbable or non-absorbable (optionally with additives) thermoplastic polymer, for example from a polylactide (PLA) or polymethyl methacrylate (PMMA).

FIG. 3 also shows the two-part negative mold in addition to the core element 1 and two anchoring elements 11 of the above-described type. The two mold parts 21, 22, separated along a separation plane, together form the negative mold. The negative mold is manufactured from an elastic material, for example a silicone substance. By bringing together the two parts 21, 22 of the negative mold, a cavity 23 with the shape of the implant to be produced with all structures is created in the interior thereof, i.e. more particularly with the energy direction transmitters as well. The mold parts 21, 22 can also have mold centering means (positioning aids), by means of which their relative position can be precisely defined. In this case, the positioning aids have the shape of conical positioning lugs 25 of the first mold part, which engage into corresponding recesses (not illustrated) of the second mold part when being brought together.

In order to carry out the deformation and/or adhering process, the core element and the anchoring elements are inserted into the negative mold in the intended position and orientation—as shown in FIG. 3—and said negative mold is exposed to an elevated deformation temperature, for example in an oven with controllable temperature. Additionally, pressure is advantageously applied, by means of which the slightly elastic mold parts are pressed against one another. In the embodiment illustrated in FIG. 4, this occurs by means of a weight 31. However, other mechanisms by means of which pressure, e.g. hydrostatic, hydraulic or pneumatic pressure, is applied are also feasible.

Subsequently, the negative mold is slowly cooled while still in the assembled state and preferably while still under pressure. This can be brought about by reducing the oven temperature in a controlled fashion or else by removing the mold from the oven and allowing it to cool slowly at the surrounding temperature—e.g. at room temperature.

Then the created implant is removed from the mold by detaching the two mold parts from one another.

Figure 5:
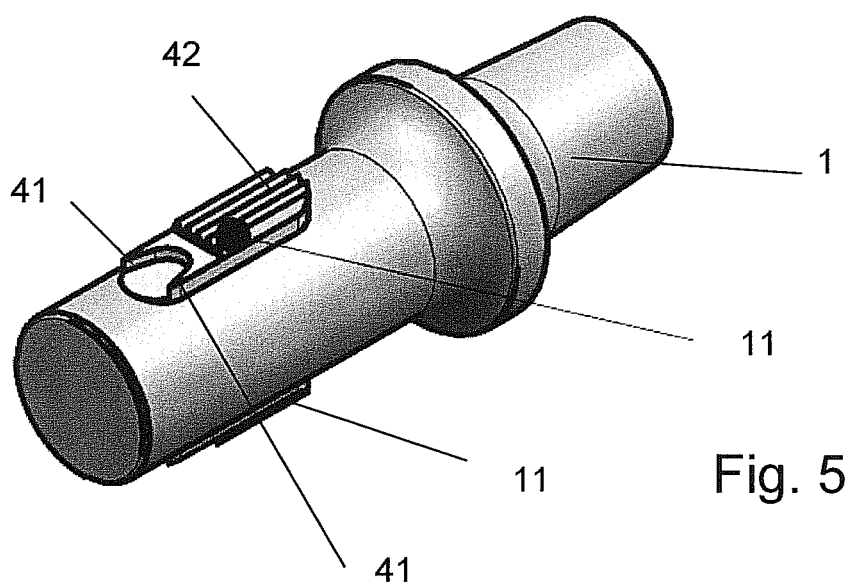
FIG. 5 shows the implant after the process.

The created implant is shown in FIG. 5. The structures now present of the anchoring element 11, which is at the top in the figure and securely adheres to the core element 1, are clearly visible in the illustrated exemplary embodiment. Energy direction transmitters in the form of two tips 41 projecting in the distal direction and ribs 42 running in the axial direction situated proximally therefrom are visible.

Example 1

In order to produce the anchoring elements, the absorbable polylactide LR706 by Boehringer Ingelheim, which is pre-pressed into plates, is used. The resomer LR706 is a mixture of L-lactide and R-polymer, the glass transition temperature is 50°-60° and the liquefaction temperature lies between 170° C. and 210° C.

Strips with appropriate external dimensions (see e.g. FIG. 2) are milled out of the plate material using a conventional milling machine. These strips serve as anchoring elements.

In order to produce a negative mold, a positive mold is modeled using a computer-aided design (CAD) system, said mold then being built layer-by-layer by stereo lithography. The positive mold created thus is filled with the two-component silicone Dublosil by Simed (often used as duplicate mass in dental technology). After the complete linking, two silicone blocks are obtained with the respective negative mold, which also have the negative or positive mold centering means (positioning aids). The Shore hardness of the two mold parts is between 24 and 26 Shore A.

The core element consists of Grade 4 titanium with a sandblasted surface with a diameter of 4 mm and an endosseous length of 10 mm. Additionally, the implant body is provided with two slots with a width of 1.5 mm, a length of 5 mm and a depth of 0.5 mm (cf. FIG. 1).

The first anchoring element is placed onto the implant body (i.e. the core element) and, together with the latter, placed into the provided mold half. The second strip is subsequently placed onto the top side of the core element and closed by the second mold half. A steel cylinder with a mass of 500 grams is used as a weight.

The whole package is heated in an incubator with convention to 130 degrees during 30 minutes and subsequently cooled for 20 minutes in the air outside the oven, but still with the weight.

This results in an implant with the desired energy direction transmitters and an excellent, intimate connection between the core element and the anchoring elements.

Example 2

Use is made of a core element like in example 1. In contrast to example 1, the anchoring elements are produced from acrylic glass XT (PMMA; glass transition temperature approximately 115° C.). The negative mold is produced from Elite double 32 silicone by Zhermack with a hardness of 32 Shore A.

The anchoring elements are, together with the core element, placed into the provided negative mold and the latter is closed. A steel cylinder with a mass of 500 grams is used as a weight.

The whole package is heated in an incubator with convention to 140 degrees during 20 minutes and subsequently cooled for 20 minutes in the air outside the oven, but still with the weight.

This likewise results in an implant with the desired energy direction transmitters and an intimate connection between the core element and the anchoring elements.

Example 3

Like example 1, but a core element made of zirconium oxide (with components of less than 10% yttrium oxide) is used as a core element. Specifically, use is made of an yttria-stabilized, tetragonal, part crystalline zirconium dioxide. Here, the utilized zirconium dioxide ceramic satisfies ISO norm 13356:2008 in respect of "implants for surgery—ceramic materials based on yttria-stabilized tetragonal zirconia (Y-TZP)".

There likewise is a good connection between the core element and the anchoring elements. As a result of the elasticity of the mold there is only a low risk of mechanical damage to the core element during the process.

Many further embodiments are feasible. Thus, for example, a negative mold may comprise a plurality of interior cavities, arranged next to one another or in matrix form or in any other regular or irregular fashion, one for each core element with the corresponding number of anchoring elements.

The invention claimed is:

1. A method for manufacturing an implant, comprising the following steps:
   providing a core element having a first material and having at least one recess with or without an undercut;
   providing a negative mold of the implant;
   providing at least one anchoring element of a second material, the second material being thermoplastic, wherein the at least one recess and the at least one anchoring element are matched to one another in terms of their number;
   positioning the core element and at least one anchoring element in a solid state in the negative mold, with the anchoring element reaching into the at least one recess,
   sealing the negative mold such that a mold internal cavity with the core element and the at least one anchoring element is formed and applying an elevated deformation temperature, wherein, at the deformation temperature, the second material is plastically deformable, viscous or liquid and the first material is solid,
   cooling the negative mold with the core element and the anchoring element, and
   removing the resulting implant, which comprises the core element and, attached thereto and anchored in the recess, the anchoring element, from the negative mold.

2. The method as claimed in claim 1, wherein the deformation temperature is greater than 37° C.

3. The method as claimed in claim 1, wherein the deformation temperature $T_D$ lies between a glass transition temperature $T_G$ and a liquefaction temperature $T_M$ of the second material with the following holding true for the deformation temperature $T_D$: $T_G + \frac{1}{4}*(T_M - T_G) < T_D < T_M$.

4. The method as claimed in claim 1, wherein a pressure is applied to the mold internal cavity, which is filled by the core element and the at least one anchoring element, at least during the application of the deformation temperature.

5. The method as claimed in claim 1, wherein in regions, the negative mold is in direct contact with the core-element surface during the application of an elevated deformation temperature.

6. The method as claimed in claim 1, wherein the negative mold has at least two mold parts which are at least partly elastic, and wherein the mold interior cavity is formable between said parts.

7. The method as claimed in claim 6, wherein the mold parts have a Shore A hardness of between 15 and 60, at least in the region of a boundary between the mold parts.

8. The method as claimed in claim 1, wherein the negative mold with the core element and the at least one anchoring element is held at the deformation temperature during a holding time of between 5 minutes and 1 hour.

9. The method as claimed in claim 1, wherein in addition to the core element, a plurality of anchoring elements are introduced into the mold internal cavity, which anchoring elements are separate from one another even after removing the implant from the core element.

10. The method as claimed in claim 1, wherein the core element is roughened and/or provided with macroscopic structures, at least in the region of a contact face with the anchoring element.

11. The method as claimed in claim 1, wherein a surface of the anchoring element is activated by means of plasma or a primer.

12. The method as claimed in claim 1, wherein the mold internal cavity has a structure in the region of the at least one anchoring element, which structure differs from a shape of the at least one anchoring element in the initial state and which structure defines at least one energy director of the anchoring element on the resulting implant.

* * * * *